United States Patent [19]

Beard

[11] Patent Number: 4,815,313

[45] Date of Patent: Mar. 28, 1989

[54] SYRINGE PRESSURE CALIBRATION REFERENCE

[75] Inventor: Robert W. Beard, Placerville, Calif.

[73] Assignee: Abbott Laboratories, Abbott Park, Ill.

[21] Appl. No.: 120,874

[22] Filed: Nov. 16, 1987

[51] Int. Cl.[4] .............................................. G01L 27/00
[52] U.S. Cl. ........................................ 73/4 R; 73/4 V
[58] Field of Search ................. 73/4 R, 4 V, 714; 604/118; 128/672, 673, 675, 674, 748

[56] References Cited

U.S. PATENT DOCUMENTS

| | | | |
|---|---|---|---|
| 2,576,687 | 11/1951 | Krehbiel | 73/714 |
| 4,051,712 | 10/1977 | Zias et al. | 73/4 R |
| 4,384,470 | 5/1983 | Fiore | 73/4 R |
| 4,658,829 | 4/1987 | Wallace | 73/4 R |
| 4,664,635 | 5/1987 | Hermann | 73/4 R |

*Primary Examiner*—Jerry W. Myracle
*Assistant Examiner*—Robert A. Raevis
*Attorney, Agent, or Firm*—Christensen, O'Connor, Johnson & Kindness

[57] ABSTRACT

A compact, inexpensive, and lightweight pressure calibrator and a method for calibrating pressure monitoring devices. The pressure calibrator (10) comprises a plunger (14) sized to slide snugly within a hypodermic syringe barrel (12). Included within the plunger are pressure transducer (56), a microprocessor (54) and other electronic components (62). A digital display (30) disposed within the side of the plunger is operative to display the pressure developed within the syringe barrel (12) as the operator moves the plunger. "O" rings (28) provide a hermetic seal between the plunger and the internal bore (16) of the syringe barrel. A tube (22) is connected to the output port (20) of the syringe and provides fluid communication between the syringe and a pressure monitoring device (26) being calibrated.

20 Claims, 4 Drawing Sheets

*Fig. 6.*

- 140 START
- 142 A TO D "ZERO" READING ON PRESS. TRANDUCER
- 144 "ZERO" READING → DISPLAY
- 146 A TO D PRESSURE READING ON PRESSURE TRANSDUCER
- 148 HAS PRESSURE CHANGED?
- 150 UPDATE PRESSURE
- 152 IS ALTERNATE UNITS SWITCH SET?
- 154 CONVERT PRESSURE TO ALTERNATE UNITS
- 156 CHECK BATTERY STATUS
- 158 DISPLAY PRESSURE AND BATTERY STATUS
- 160 STOP

SYRINGE PRESSURE CALIBRATION REFERENCE

FIELD OF INVENTION

The present invention generally pertains to a pressure calibration device, and specifically to a device for calibrating pressure transducers at relatively low gauge pressures, by producing a known reference pressure.

BACKGROUND OF THE INVENTION

Relatively inexpensive solid state pressure transducers are routinely used for monitoring the cardiovascular pressure and other fluid pressures of patients who are hospitalized or undergoing medical treatment and diagnostic tests. The accuracy of these pressure monitoring devices is subject to change, possibly producing substantial errors in the indicated pressure. In certain critical procedures where the patient's physiological state must be accurately monitored, errors in a pressure transducer connected to monitor a vital body function may become very significant, even life-threatening in their consequences.

Calibration of such pressure monitoring devices may be accomplished by comparison against a reference standard to which the same fluid pressure is applied. Ideally, the pressure transducer under test should be calibrated at a minimum of three reference points, including its full scale rated pressure, to determine its accuracy and linearity. Although a more accurate reference standard such as an air piston gauge may be used, a digital readout pressure reference standard is available for this purpose. The device is approximately the same size as a hand calculator and weighs several pounds. This reference standard is designed to supply a variable calibration pressure to a pressure transducer under test. Adjustment of the calibration pressure is effected by turning a thumb wheel to vary the fluid displacement of a piston in a cylinder.

Although relatively small, the above-described prior art pressure transducer reference standard is too bulky to be conveniently carried on the person of a nurse or medical technician. In addition, its cost makes it impractical to equip each individual having a need to check pressure monitors with the device. Unfortunately, experience has shown that unless a reference standard is readily at head, pressure transducers used in critical medical applications are unlikely to be calibrated as often as should be. With the growing concern about medical malpractice, it has become very important for hospitals, doctors and health care personnel to take all reasonable steps to ensure the patient's wellbeing. Such reasonable steps would probably include frequently checking the accuracy of pressure monitoring devices used to monitor critical bodily functions.

In consideration of these concerns, it is an object of the present invention to provide a low cost, portable calibration reference, useful for calibrating pressure monitoring devices.

It is a further object to provide an easily adjusted calibration pressure that may be readily input to the pressure monitoring transducer.

A still further object is to provide a known calibration reference pressure with a compact device, sufficiently small and lightweight to be carried on the person of a user.

Yet a still further object is to provide a digital display on a calibration reference standard, indicating the pressure of the fluid supplied to calibrate the pressure monitoring device.

These and other objects of the invention will be apparent from the description of the preferred embodiment of the invention in relation to the attached drawings.

SUMMARY OF THE INVENTION

The present invention is directed to an apparatus useful for calibrating pressure sensing devices by supplying a fluid at a known pressure. The apparatus comprises a plunger, adapted for use with a syringe having an output port connected through a line in fluid communication with a device to be calibrated. The plunger, sized to slide snugly inside the syringe, is inserted therein, and a force is applied to the outwardly extending end of the plunger by an operator to develop a desired calibration pressure. A calibration pressure less than local atmospheric pressure is developed by pulling outwardly on the end of the plunger. Alternatively, a calibration pressure in excess of local atmospheric pressure may be developed by forcing the plunger inwardly of the syringe.

The plunger includes a hermetic seal disposed around its outer circumference, adapted to engage to the inner surface of the syringe. The seal, preferably an "O" ring, reduces or eliminates fluid leakage between these surfaces as the plunger is moved inside the syringe. A pressure transducer is disposed within the syringe, exposed to the fluid pressure developed by the operator-applied force. The pressure transducer produces a signal proportional to the pressure developed within the syringe and the attached line. Connected to the pressure transducer inside the plunger are processor means. The processor means are operative to drive a digital display that is also disposed within the plunger, on which the calibration pressure developed by the operator is displayed. This calibration pressure is communicated through the fluid line to the pressure monitoring device being calibrated, for comparison to its indicated pressure.

BRIEF DESCRIPTION OF THE DRAWINGS

FIG. 6 is a flowchart illustrating the logic of the control algorithm used in providing a digital display of calibration pressure.

DESCRIPTION OF THE PREFERRED EMBODIMENT

Figure 1:
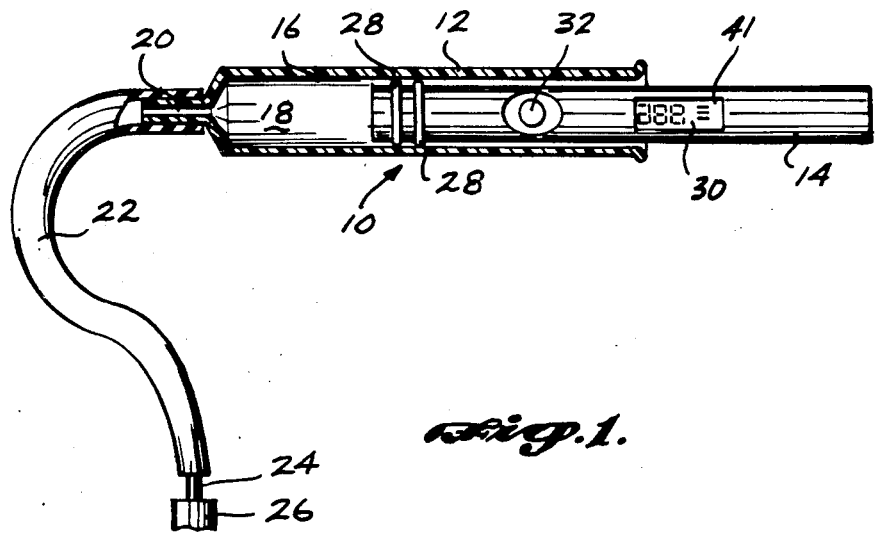
FIG. 1 illustrates a cutaway side view of a syringe, showing how a preferred embodiment of the present invention is fitted therein.

With reference to FIG. 1, a pressure calibrator constructed in accordance with the present invention is generally denoted by reference numeral 10. Pressure calibrator 10 includes a generally conventional plastic (or glass) hypodermic syringe barrel 12 and a plunger 14 sized to fit snugly within the internal bore 16 of the syringe barrel. When inserted into syringe barrel 12 as shown in FIG. 1, the inwardly extending end of plunger 14 defines one end of a chamber 18 containing a fluid. Normally this fluid comprises air, although liquids and other gaseous fluids may be used.

An output port 20 is defined by the end of syringe barrel 12, where it necks down to a relatively small diameter cylindrical surface on which a hypodermic needle would be fitted if the syringe were used conventionally. Instead, one end of a length of tubing 22 is fitted over output port 20, and the other end is attached to a reference pressure port 24 of a pressure monitoring device that is to be calibrated, providing a fluid communication path between chamber 18 and the pressure monitoring device 26.

Just as movement of the solid plastic or glass plunger normally used with a hypodermic syringe is operative to change the volume within the syringe, forcing fluid through an attached needle, movement of plunger 14 within syringe barrel 12 changes the volume of chamber 18. Furthermore, as the volume of chamber 18 changes, the pressure of fluid within the chamber and tubing 22 changes proportionally. Whenever plunger 14 is partially withdrawn from the internal bore 16 of syringe barrel 12, the volume of chamber 18 is increased, and the pressure of fluid within the chamber and within tubing 22 is reduced. Conversely, as a force applied to the end of plunger 14 (in alignment with its longitudinal axis) causes it to move further into the internal bore 16 of the syringe barrel, the volume of chamber 18 decreases, with a concomitant increase in pressure of the fluid contained therein.

Two "O" rings 28 are fitted within grooves formed on the outer surface of plunger 14, providing a hermetic seal between the outer surface of the plunger and the internal bore 16 of syringe barrel 12. "O" rings 28 substantially eliminate leakage of fluid between these surfaces as plunger 14 is moved within syringe barrel 12. It may also be possible to provide an adequate seal with only one "O" ring 28.

Disposed on the side of plunger 14 are a pushbutton switch 32 and a digital display 30. Pushbutton switch 32 is centered in a depression within the cylindrical surface of plunger 14, inset sufficiently so that the top of the pushbutton does not contact the internal bore 16 of syringe barrel 12 when plunger 14 is inserted therein. Digital display 30 has 2 ¾ digits of resolution, i.e., it is capable of displaying a reading in the range ±399.

Figure 2:
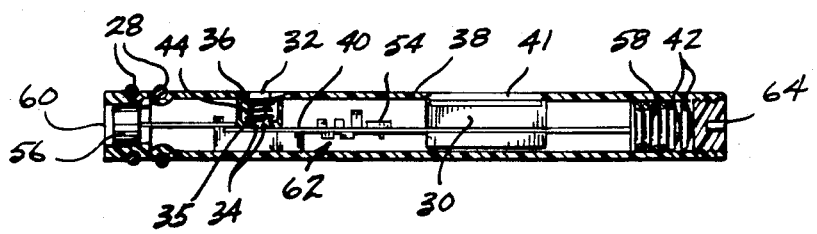
FIG. 2 illustrates a plunger comprising the present invention in longitudinal cross-sectional view.

Turning now to FIG. 2, a cross-section of plunger 14 illustrates details of the internal construction of the plunger. Plunger 14 comprises a cylinder 38 formed from plastic or a metal such as brass. Cylinder 38 is shorter and approximately the same diameter as a conventional ball point pen, and is readily carried on the person of a user, e.g., in a breast pocket of a shirt. A printed circuit card 40 is disposed along the longitudinal axis of cylinder 38, centered therein and extending diametrically across the cylinder. A plurality of electronic components generally denoted by reference numeral 62 are mounted on printed circuit board 40, including a microprocessor 54. Digital display 30 is also mounted upon printed circuit board 40, positioned immediately below a plastic window 41 that is fitted into an opening within cylinder 38. The window has substantially the same radius of curvature as the external surface of the cylinder.

A plug 64 is threaded into one end of plunger 14. Plug 64 is removable to provide access to a pair of button or disc-shaped lithium batteries 42, which provide power for electronic components 62. Under normal intermittent usage, lithium batteries 42 are expected to provide power for the components 62 for up to five years; however, plug 64 may be removed so that the batteries can be replaced or so that electronic components 62 may be serviced. A spring 58 is connected to the adjacent end of printed circuit board 40, providing an electrical connection between a conducting trace (not shown) on the printed circuit board and the case of one of the batteries 42. In addition, spring 58 provides a biasing force to ensure good electrical contact between the spring and battery, and between the two batteries. The center of the other battery 42 contacts a conducting surface (not shown) that is also connected to the printed circuit board 40.

Pushbutton switch 32 includes a conducting surface 35 disposed adjacent a pair of spaced apart electrical contacts 34 on printed circuit board 40. Depression of the pushbutton completes the circuit between contacts 34 th rough conducting surface 35, energizing electronic components 62 as will be described in greater detail hereinbelow. Pushbutton switch 32 also includes a helical spring 44 to bias surface 35 away from contacts 34; a flange 36 formed around the perimeter of the pushbutton abuts the interior surface of cylinder 38, serving the retain the pushbutton inside cylinder 38.

Figure 3:
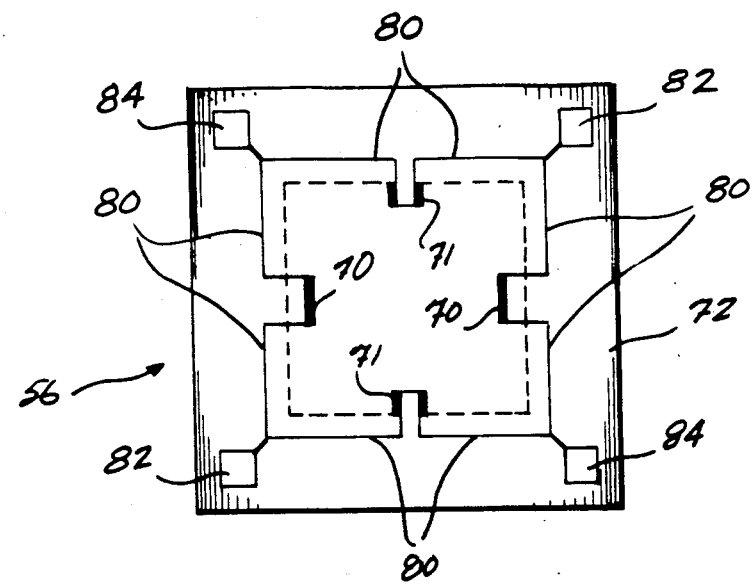
FIG. 3 is a schematic representation of a solid state pressure transducer used in the plunger of the preferred embodiment.
Figure 4:
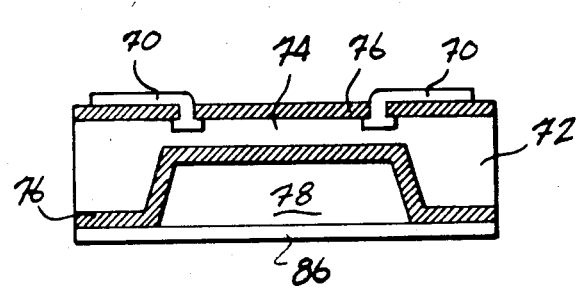
FIG. 4 shows the solid state pressure transducer of FIG. 3 in a cross-sectional view.

The end of cylinder 38 that is inserted into syringe barrel 12 (on the left as shown in FIG. 2) defines a port 60 through which pressurized fluid is applied to a pressure transducer 56 mounted inside the cylinder, adjacent port 60. Details of pressure transducer 56 are shown in FIGS. 3 and 4. The pressure transducer used in the preferred embodiment is a conventional piezoresistive silicon sensor, including P-type regions comprising sensing resistors 70 and 71, disposed in an N-type silicon wafer 72. The center of the N-type silicon wafer 72 is a relatively thin silicon diaphragm 74. Layers of silicon oxide 76 insulate the surfaces of silicon wafer 72. During manufacture, its bottom surface is joined to a plate 86 (while within a vacuum environment), forming a vacuum chamber 78 between plate 86 and the center silicon diaphragm 74 of the wafer.

The P-type regions comprising sensing resistors 70 and 71 are disposed in silicon wafer 72 adjacent the top surface of silicon diaphragm 74, around the edge of vacuum chamber 78, and the connected by conductors 80 in a standard Wheatstone bridge circuit. Application of fluid pressure to silicon diaphragm 74 causes it to deflect, changing the relative resistance of the sensing resistors 70 and 71. When exposed to a vacuum, no pressure is applied to the silicon diaphragm, and the resistance of resistors 70 and 71 are substantially equal since the Wheatstone bridge is in a balanced condition. If a voltage is applied to nodes 84 at diagonally opposite corners of the bridge, the potential difference between nodes 82 at the other two corners is then approximately zero. Conversely, when the center of silicon diaphragm 74 is deflected by an applied fluid pressure, the potential difference between nodes 82 changes in direct proportion to the pressure, the resistance of sensing resistors 70 increasing, and the resistance of sensing resistors 71 decreasing by equal amounts, creating an imbalanced condition of the Wheatstone bridge. With voltage applied to nodes 84, pressure transducer 56 then provides an output voltage between nodes 82 that is proportional to the pressure applied to center silicon diaphragm 74 of the transducer.

Those skilled in the art will appreciate that other types of pressure transducers might be used in this application. For example, a transducer responding to pressure by changing capacitance, thus varying the resonant frequency of a connected circuit, would be suitable. Any such pressure transducer used should have a rated accuracy at least equivalent to that of the pressure monitoring devices likely to be calibrated, and should produce a voltage, current, or some other physical parameter that changes as a function of the applied pressure, in the desired range. In the preferred embodiment, pressure transducer 56 has a rated accuracy of ±1% of the applied pressure and is rated to measure pressures of at least ±400 mm. of mercury.

Figure 5:
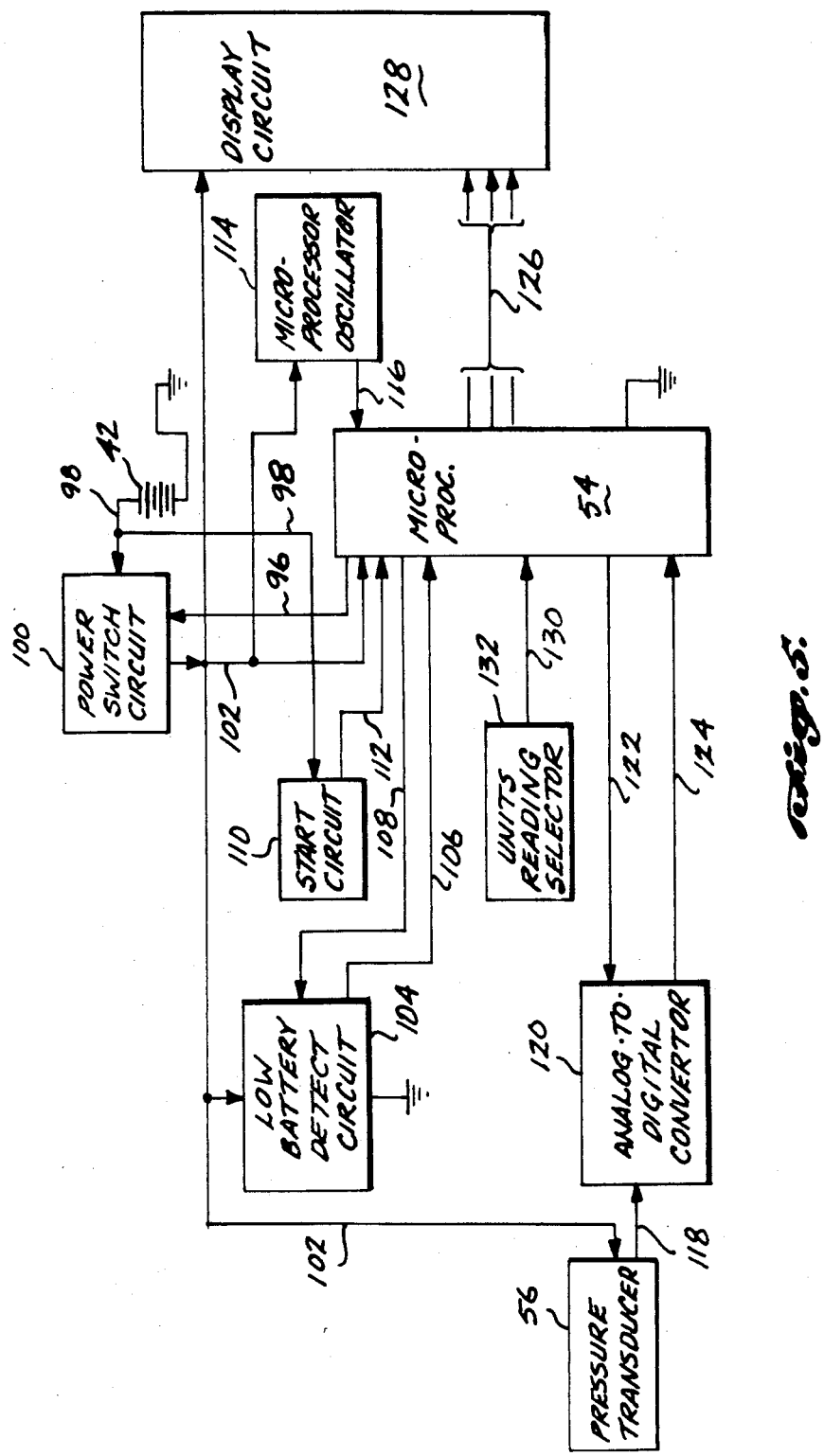
FIG. 5 is a functional block diagram of the electrical circuit used in the preferred embodiment of the present invention.

Referring now to FIG. 5, a block diagram shows the relationship between the various electronic components 62 of pressure calibrator 10. Power for the electronic components used in the circuit represented in FIG. 5 is supplied by batteries 42, connected to ground and to a power switching circuit 100, by a conductor 98. Power switching circuit 100 controls the application of DC voltage to each of the other elements of the pressure calibrator in response to a signal provided over a conductor 96 from microprocessor 54. In the preferred embodiment, an internal timer within microprocessor 54 resets and counts down for a predetermined interval each time pushbutton switch 32 is depressed, so that battery power is applied to the electronic components of pressure calibrator 10 only for 90 seconds, thereby ensuring that batteries 42 are not run-down by someone inadvertently leaving the device energized for an extended period of time. A transistor switch (not shown) or other type of electronic switch may be used to carry out the functions of power switching circuit 100, as will be apparent to those of ordinary skill in the art. Conductor 98 also conveys DC power from batteries 42 to a start circuit 110. Start circuit 110 includes pushbutton switch 32, which when depressed, applies DC voltage through conductor 112 to reset the internal counter within microprocessor 54. In response to the signal from microprocessor 54 initiating the 90 second timed period, DC power is applied via conductor 102 to a display circuit 128, microprocessor 54, a low battery detect circuit 104 and to pressure transducer 56.

Low battery detect circuit 104 is operative to compare the DC voltage on conductor 102 to a reference voltage derived from a batter check signal supplied by microprocessor 54 to the low battery detect circuit over conductor 108. The battery check signal is clamped at approximately 0.6 volts DC using a diode (not shown) and compared to a voltage obtained by a divider circuit (not shown) from the battery power supply. Such low battery detect circuits are well known to those of ordinary skill in the art. The result of the battery voltage check performed by the low battery detect circuit 104 is returned to microprocessor 54 via conductor 106.

A microprocessor oscillator 114 is provided for use as a time base my microprocessor 54. In the preferred embodiment, microprocessor oscillator 114 simply comprises an RC circuit. Alternatively, a crystal oscillator could be used; however, the accuracy of a crystal is not required in this application. The time base signal provided by microprocessor oscillator 114 is input to microprocessor 54 through a conductor 116.

A plurality of data lines 126 connect microprocessor 54 to a display circuit 128, comprising the 2 ¾ digital display 30 and a appropriate driver chip (not separately shown). Data provided via data lines 126 are used by the display driver to energize selected digits of digital display 30, indicating the pressure sensed by pressure transducer 56 as will be explained hereinbelow.

An optional unit reading selector 132, comprising a jumper wire (not shown) or other suitable switching device is provided on printed circuit board 40 (FIG. 2) to change the units of pressure indicated by digital display 30 from the "normal units," millimeters of mercury, to inches of water column (or some other units of pressure). Unit reading selector 132 provides a means for selecting the "optional" units of pressure by grounding an input port of microprocessor 54 through conductor 130. It is not contemplated that a change in pressure units should be readily available to an operator of pressure calibrator 10.

The heart of the pressure calibrator is the pressure transducer 56. As explained above, it produces a DC voltage proportional to an applied fluid pressure. This voltage is output via conductor 118 to analog-to-digital converter 120. Although various analog-to-digital converter chips are commercially available, in the preferred embodiment, analog-to-digital converter 120 implements a dual slope integrator technique in which an internal counter within microprocessor 54 accumulates counts in a register for a period of time proportional to the voltage output by pressure transducer 56. Initiation of the analog-to-digital conversion process begins with a signal output by microprocessor 54 over conductor 122 to analog-to-digital converter 120 and terminates in response to a signal from analog-to-digital converter 120 input to microprocessor 54 via conductor 124. Other techniques and commercially available A-D converter integrated circuits suitable for providing 2 ¾ digit resolution and 1% accuracy might also be used for this application, as will be apparent to those of ordinary skill in the art.

Microprocessor 54 preferably comprises a National Semiconductor Corporation model COP 411-C CMOS microcontroller. It is anticipated that similar microprocessors may be used for this application, preferably those with relatively low power consumption, to ensure extended battery life. Included within microprocessor 54 is a read only memory (ROM), in which a series of machine language instructions are stored for carrying out each of the steps implemented by the microprocessor, including: checking the battery condition, carrying out the analog-to-digital conversion process to digitize the pressure responsive signal produced by the pressure transducer, converting the digitized signal to a pressure, applying the selected units to the pressure measured by pressure transducer 56, and displaying the pressure on digital display 30. Microprocessor 54 also includes random access memory (RAM) for temporarily storing variables used in carrying out these functions.

A flowchart illustrating the algorithm implemented by microprocessor 54 is shown in FIG. 6. Beginning with block 140, the control logic "starts" with the depression of pushbutton switch 32, initiating the 90 second internal countdown timer. In block 142, microprocessor 54 implements the analog-to-digital conversion of the signal output from the pressure transducer via conductor 122 (FIG. 5). Initially, pressure transducer 56 is exposed to atmospheric pressure so that microprocessor 54 can establish a Zero Pressure reading, as indicated in block 144.

In block 146, the analog-to-digital conversion process is again implemented, after the pressure applied to pressure transducer 56 has changed from the initial atmospheric pressure as checked in block 148. The value of the variable, "Pressure," is updated to reflect the new reading in block 150. Following the step in block 150, (or if the result of the check made in block 148 is negative), in block 152, microprocessor 56 determines if the alternate units switch has been set, and if so, in block 154, converts the value for Pressure to an equivalent valve in the alternate units. This conversion is done by multiplying Pressure by the appropriate conversion factor. Of course, if the alternate unit switch has not been set, block 154 is skipped, control logic proceeding directly to block 156. In block 156, the condition of the batteries 42 is checked by low battery detect circuit 104, in response to a signal produced by microprocessor 54.

Finally, in block 158, microprocessor 54 outputs the pressure reading to display circuit 128 via data lines 126 causing digital display 30 to indicate the pressure in the selected units, and to indicate the current battery status. Although not shown in the flow chart, should the pressure exceed the maximum rated range for pressure calibrator 10 (±399 mm of mercury) in block 158, microprocessor 54 may optionally cause digital display 30 to blink on and off while displaying the numbers 399, or alternatively may display the letters "DP" (defective pressure), or other symbols indicating a fault condition. During the 90 second period following initiation of the pressure measurement, microprocessor 54 repeats steps 146 through 158, terminating at block 160 when the 90 second period has expired.

In using pressure calibrator 10, the operator depresses pushbutton 32 on plunger 14 prior to inserting it within syringe barrel 12, permitting microprocessor 54 to autozero so that digital display 30 reads 0 mm of mercury when initially exposed to atmospheric pressure. Thereafter, plunger 14 is immediately inserted to its full extent within syringe barrel 12 and tubing 22 is connected to output port 20. Plunger 14 is partially withdrawn from syringe barrel 12, developing a pressure within chamber 18 that is less than local atmospheric pressure. This subatmospheric pressure is communicated via tubing 22 to the pressure monitoring device 26. Plunger 14 is displaced within syringe barrel 12 until the desired calibration pressure is indicated on digital display 30. This calibration pressure is then compared against the pressure indicated by pressure monitoring device 26.

Plunger 14 may be twisted within syringe barrel 12 to make small incremental changes in the indicated pressure. It has been found that static friction between "O" rings 28 and the internal bore 16 of syringe barrel 12 is sufficient to hold plunger 14 in place, once a desired calibration pressure is achieved by the operator. The calibration pressure developed in this manner is below ambient or local atmospheric pressure, as is conventional for calibrating a convention pressure monitoring device 26. Port 24 on pressure monitoring device 26 corresponds to a normally vented reference pressure port. When a subatmospheric calibration pressure is applied to reference port 24 while the port (not shown) that is normally exposed to a monitored fluid pressure is exposed to atmospheric pressure, pressure monitoring device 26 should indicate a pressure equal but opposite in sign to the pressure shown on digital display 30. Comparison of the display 32 on pressure calibrator 10 with the pressure indicated by pressure monitoring device 26 determines the error of the device.

Pressure calibrator 10 may also be used to generate calibration pressures that are greater than local atmospheric pressure. As before, pushbutton switch 32 is depressed prior to inserting plunger 14 into syringe barrel 12, auto zeroing the reading. Plunger 14 is inserted into syringe barrel 12 until a seal is obtained between the "O" rings 28 and the syringe bore 16, and tubing 22 is connected to output port 20. Sufficient force is then applied against the end of plunger 14 (directed along its longitudinal axis) to obtain a desired calibration pressure indication on digital display 30 as the plunger slides into the syringe barrel. Using this technique, a calibration pressure in excess of local atmospheric pressure is developed within chamber 18 and applied to the port (not shown) of pressure monitoring device 26 that is normally used to monitor pressure. The latter technique is also useful in calibrating pressure monitoring devices that do not include a readily accessible reference port 24.

While the present invention has been described with respect to a preferred embodiment, those skilled in the art will understand that various changes and modifications thereto may be made within the scope of the claims that follow hereinbelow.

The embodiments of the invention in which an exclusive property or privilege is claimed are defined as follows:

1. Apparatus for producing a desired fluid pressure in a fluid line connected to an output port of a syringe, comprising: a plunger, adapted to slide snugly inside a barrel of the syringe when a force is applied to one end of the plunger by an operator, said plunger including:
   a. a sliding hermetic seal disposed between an outer surface of the plunger and an inner surface of the syringe;
   b. a pressure transducer disposed within the plunger, the pressure transducer being exposed to fluid pressure developed inside the syringe by the operator applied force and operative to produce a signal proportional to said fluid pressure;
   c. a digital display disposed within the plunger; and
   d. processor means, disposed within the plunger and connected to the pressure transducer and the digital display, for driving the digital display to indicate the fluid pressure developed in the syringe as a function of the signal, so that the operator may apply sufficient force to the plunger to develop the desired fluid pressure in the fluid line, as indicated on the digital display.

2. The apparatus of claim 1, wherein the plunger is generally cylindrical in shape, and wherein the sliding hermetic seal comprises an "O" ring disposed concentrically around the plunger.

3. The apparatus of claim 1, wherein the plunger includes a switch for selectively energizing the processor means to drive the digital display to indicate the fluid pressure for a predetermined interval of time.

4. The apparatus of claim 3, wherein the switch comprises a pushbutton disposed in the side of the plunger.

5. The apparatus of claim 1, further comprising a battery power supply disposed within the plunger.

6. The apparatus of claim 1, wherein the digital display is disposed within a sidewall of the plunger, intermediate the hermetic seal and the end of the plunger to which the operator applies the force.

7. Apparatus for producing a desired fluid pressure in a fluid line to calibrate a fluid pressure monitoring device that is connected in fluid communication with the fluid line, said apparatus comprising:
  a. cylinder means for defining a chamber having an output port adapted for connection to the fluid line, and a smooth internal bore;
  b. piston means, slidingly disposed within the smooth bore of the cylinder means and forming a hermetic seal therewith, for varying the volume of the chamber and thus controlling the pressure of fluid contained therein;
  c. pressure sensing means, disposed within the piston means, for sensing the fluid pressure in said chamber and producing a signal indicative of its magnitude;
  d. display means disposed within the piston means, for displaying the magnitude of the fluid pressure inside the chamber; and
  e. signal processing means, connected to the pressure sensing means, for processing the signal and driving the display means to display the fluid pressure inside the chamber as a function of said signal;
  f. wherein a variable force is applied to the piston means to develop a calibration pressure in the fluid line that may be used to calibrate a fluid pressure monitoring device at a plurality of test pressures.

8. The apparatus of claim 7, wherein the piston means include an "O" ring for hermetically sealing against the smooth bore of the cylinder means.

9. The apparatus of claim 7, wherein the pressure sensing means comprise a solid state pressure transducer disposed in fluid communication with the cylinder, and wherein the signal is a voltage proportional to fluid pressure in the cylinder.

10. The apparatus of claim 7, wherein the display means comprise a digital display visible through a side of the piston means.

11. The apparatus of claim 10, wherein the signal processing means comprise a microprocessor, an analog-to-digital converter for converting the signal produced by the pressure transducer to a digital value, and memory means for storing a program defining the steps by which the signal is processed by the microprocessor, to indicate the pressure in the chamber on the display means.

12. The apparatus of claim 7, wherein the piston means include an internal battery power supply and means for selectively energizing the signal processing means with the battery power supply.

13. The apparatus of claim 7, wherein the desired fluid pressure is sub-atmospheric, and wherein the variable force is applied to the piston means by an operator pulling an end of the piston means outwardly of the cylinder means, the operator of the apparatus exerting sufficient force in a direction aligned with a longitudinal axis of the piston means to achieve indication of the desired fluid pressure on the display means.

14. The apparatus of claim 7, further comprising a reset switch wherein the signal processing means for operative to drive the display means only for a predetermined interval of time after the reset switch is actuated.

15. A method for calibrating a fluid pressure monitoring device connected in fluid communication with a fluid line, said fluid pressure monitoring device being operative to produce an indication of fluid pressure in the fluid line, comprising the steps of:
  a. slidingly fitting a pressure transducer reference standard inside a syringe, the reference standard being disposed in a case having at least a portion thereof sized to fit within the syringe in a close fit for use as a plunger, said case including an electronic digital pressure display indicating the pressure to which the pressure transducer reference standard is exposed;
  b. connecting an output port of the syringe to the fluid line;
  c. applying a force directed along the longitudinal axis of the pressure transducer reference standard by either: (i) pushing the pressure transducer reference standard into the syringe, compressing the fluid in the syringe to produce a fluid pressure inside the fluid line in excess of ambient atmospheric pressure, or (ii) pulling the pressure transducer reference standard partially out from the syringe to produce a fluid pressure in the fluid line that is less than ambient atmospheric pressure; the displacement of the pressure transducer reference standard in the syringe producing a calibration fluid pressure in the fluid line, the magnitude of which is indicated on the digital pressure display; and
  d. comparing the pressure indicated on the digital pressure display of the pressure transducer reference standard with the pressure indicated by the pressure monitoring device to determine the error of the pressure monitoring device.

16. The method of claim 15, wherein the pressure transducer reference standard comprises a reference pressure transducer operative to produce a signal, a mircroprocessor for processing the signal causing the digital pressure display to indicate the pressure in the syringe, and an electronic memory in which is stored a program defining the steps that the microprocessor carries out in processing the signal.

17. The method of claim 15 wherein the pressure transducer reference standard comprises a cylinder having an "O" ring concentric thereto, used to form a sliding hermetic seal between the pressure transducer reference standard and an internal bore of the syringe.

18. The method of claim 17, wherein the fluid line is connected to a normally vented reference port on the fluid pressure monitoring device.

19. The method of claim 15, wherein the fluid pressure monitoring device is normally used to monitor the pressure of bodily fluids.

20. The method of claim 15, further comprising the step of initially energizing the pressure transducer reference standard when it is outside the syringe to autozero the digital pressure display.

* * * * *

UNITED STATES PATENT AND TRADEMARK OFFICE
CERTIFICATE OF CORRECTION

PATENT NO. : 4,815,313
DATED : March 28, 1989
INVENTOR(S) : Robert W. Beard

It is certified that error appears in the above-identified patent and that said Letters Patent is hereby corrected as shown below:

| Column | Line | Error |
|--------|------|-------|
| 1 | 47 | "head," should be --hand,-- |
| 1 | 52 | "wellbeing" should be --well-being-- |
| 3 | 51 | "cross-section" should be --cross section-- |
| 4 | 23 | "th rough" should be --through-- |
| 4 | 52 | "resistance" should be --resistances-- |
| 5 | 14 | "$\pm$ 196" should be $\pm$ 1%-- |
| 5 | 49 | "batter" should be --battery-- |
| 7 | 6 | "150," should be --150-- |
| 7 | 11 | "valve" should be --value-- |
| 7 | 57 | "convention" should be --conventional-- |
| 9 | 52 | "sub-atmospheric" should be --subatmospheric-- |
| 9 | 61 | "for" should be --are-- |

Signed and Sealed this

Tenth Day of October, 1989

*Attest:*

DONALD J. QUIGG

*Attesting Officer*  *Commissioner of Patents and Trademarks*